(12) United States Patent
Kozicki (10) Patent No.: US 10,558,172 B2
(45) Date of Patent: Feb. 11, 2020

(54) TIMING DEVICE USING ELECTRODEPOSIT GROWTH

(71) Applicant: ARIZONA BOARD OF REGENTS ON BEHALF OF ARIZONA STATE UNIVERSITY, Scottsdale, AZ (US)

(72) Inventor: Michael N. Kozicki, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 130 days.

(21) Appl. No.: 15/760,907

(22) PCT Filed: Oct. 5, 2016

(86) PCT No.: PCT/US2016/055454
§ 371 (c)(1),
(2) Date: Mar. 16, 2018

(87) PCT Pub. No.: WO2017/062425
PCT Pub. Date: Apr. 13, 2017

(65) Prior Publication Data
US 2018/0259911 A1    Sep. 13, 2018

Related U.S. Application Data

(60) Provisional application No. 62/237,408, filed on Oct. 5, 2015.

(51) Int. Cl.
*G04F 13/04* (2006.01)
*G01N 27/42* (2006.01)
*G04F 1/02* (2006.01)

(52) U.S. Cl.
CPC ............. *G04F 13/04* (2013.01); *G01N 27/42* (2013.01); *G04F 1/02* (2013.01)

(58) Field of Classification Search
CPC ............ G04F 1/02; G04F 13/04; G01N 27/42
See application file for complete search history.

(56) References Cited

U.S. PATENT DOCUMENTS 3,090,914 A  *  5/1963  Kabak ..................... G01N 27/42
                                                    368/114
3,210,662 A  *  10/1965  Steinmetz .............. G01R 22/02
                                                    324/94

(Continued)

OTHER PUBLICATIONS

International Search Report and Written Opinion for Application No. PCT/US2016/055454 dated Jan. 17, 2017, 9 pages.

(Continued)

*Primary Examiner* — Edwin A. Leon
*Assistant Examiner* — Jason M Collins
(74) *Attorney, Agent, or Firm* — Michael Best & Friedrich LLP (57) ABSTRACT

Systems and methods are presented for a timing device. The timing device includes a first electrode, a second electrode, and an electrolyte. The electrolyte includes a material selected such that an electrodeposit forms on the first electrode when a current is applied between the first electrode and the second electrode. A measurable electrical characteristic of the timing device is indicative of a time-dependent degree of growth of the electrodeposit between the first electrode and the second electrode.

18 Claims, 7 Drawing Sheets

(56) References Cited

U.S. PATENT DOCUMENTS

| | | | | |
|---|---|---|---|---|
| 4,367,957 A * | 1/1983 | Bradley | ............... | G07C 1/30 |
| | | | | 116/200 |
| 4,473,806 A | 9/1984 | Johnston | | |
| 5,273,641 A | 12/1993 | Blechta et al. | | |
| 6,198,701 B1 | 3/2001 | De Jonghe et al. | | |
| 10,250,062 B2 * | 4/2019 | Chen | ............... | H02J 7/025 |
| 2007/0064541 A1 * | 3/2007 | Kagan | ............... | G04F 1/005 |
| | | | | 368/108 |
| 2008/0094076 A1 | 4/2008 | Hibbs et al. | | |
| 2009/0081553 A1 * | 3/2009 | Kondo | ............... | H01M 2/021 |
| | | | | 429/314 |
| 2013/0163392 A1 | 6/2013 | Braunberger | | |

OTHER PUBLICATIONS

Kozicki et al., "Applications of Programmable Resistance Changes in Metal-Doped Chalcogenides," Electrochem. Soc, 1999; 99:298-309.

Manne et al., "Atomic-resolution electrochemistry with the atomic force microscope: copper deposition on gold," Science, 1991; 251:183-186.

Timalsina et al., "Effects of nanoscale surface roughness on the resistivity of ultrathin epitaxial copper films," Nanotechnology, 2015; 26:1-10.

* cited by examiner

TIMING DEVICE USING ELECTRODEPOSIT GROWTH

RELATED APPLICATIONS

This Application claims the benefit of U.S. Provisional Patent Application No. 62/237,408, filed Oct. 5, 2015, entitled "NON-VOLATILE TIMING DEVICE," the entire contents of which are incorporated herein by reference.

BACKGROUND

The present invention relates to a timing device that can be used in various different applications to monitor an elapsed time duration including, for example, a "fuse" timer for delayed activation of a device/function or as an "odometer" for monitoring a total run-time of a device/system.

SUMMARY

Embodiments of the invention provide a timing device that uses changes in electrical parameters caused by the controlled growth of a conductive metallic electrodeposit on a high resistance solid electrolyte film between multiple electrodes. The length of the electrodeposit alters the resistance and capacitance of the structure and since it grows at a rate that is determined by the magnitude of the current supplied to the device, the effect can be used for timing purposes, including fuses in weapons or "odometers" (e.g., run timers) in electronic systems, including integrated circuits. The electrodeposit is persistent and so the timing function is non-volatile, i.e., the state of the timer is preserved if the system is powered-down. The timing device does not contain electronic or mechanical counters to accomplish a timing operation.

In one embodiment, the invention provides a timing device including a first electrode, a second electrode, and an electrolyte. The electrolyte includes a material selected such that an electrodeposit forms on the first electrode when a current is applied between the first electrode and the second electrode. A measurable electrical characteristic of the timing device is indicative of a time-dependent degree of growth of the electrodeposit between the first electrode and the second electrode.

In another embodiment, the invention provides a method of operating a timing device. A current is applied between a first electrode and a second electrode. The first electrode and the second electrode are coupled by an electrolyte that includes a material that causes an electrodeposit to form on the first electrode when the current is applied. An output signal indicative of growth of the electrodeposit between the first electrode and the second electrode is monitored and an output timing signal indicative of expiration of a timer is generated when the output signal indicative of growth of the electrodeposit passes a defined threshold.

In some embodiments, the invention provides a timing device comprising an anode, a cathode, a substrate extending between the anode and the cathode and in contact with an electrolyte, an electrical current source in communication with the anode and the cathode, the electrical current source configured to control the formation of an electrodeposit on the substrate and a sensing electrode positioned between the anode and the cathode, the sensing electrode configured to detect changes in electrical characteristics of the electrodeposit.

In other embodiments, the invention provides a method of using a timing device comprising controlling the formation of an electrodeposit on a substrate with an electrical current source in communication with an anode and a cathode, wherein the substrate extends between the anode and the cathode and is in contact with an electrolyte and detecting changes in electrical characteristics of the electrodeposit with a sensing electrode, wherein the sensing electrode is positioned between the anode and the cathode.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
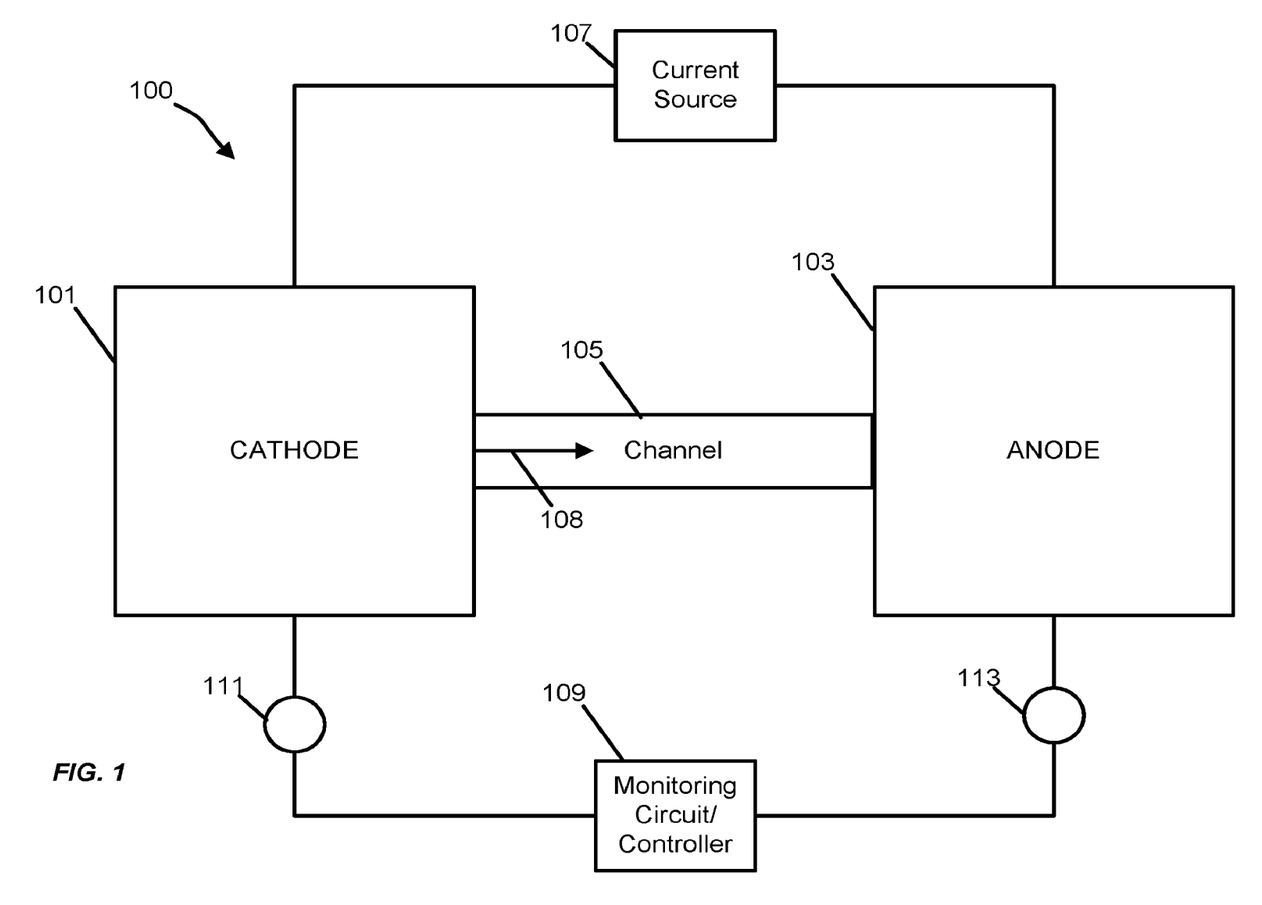
FIG. 1 is a schematic block diagram of a timing device that generates and monitors electrodeposit growth as a timing mechanism according to one embodiment.

FIG. 1 illustrates an example of a timing device 100 that uses changes in electrical parameters caused by the controlled growth of a conductive metallic electrodeposit on a high resistance solid electrolyte film. A cathode 101 and an anode 103 are coupled to opposite ends of a channel 105. An electrolyte material is positioned in the channel 105 (or, in some embodiments, the channel 105 is formed in the electrolyte material. The high resistance solid electrolyte film is placed in contact with both the cathode 101 and the anode 103. When a current between the cathode 101 and the anode 103 is applied by a current source 107, an electrodeposit 108 forms on the cathode 101. The electrodeposit 108 continues to grow within the channel 105 toward the anode 103.

The length of the electrodeposit alters various measurable electrical characteristics of the timing device 100 including the resistance and capacitance of the structure. Because the electrodeposit grows at a rate that is relative to the magnitude of the current supplied to the device, changes in the measurable electrical characteristics can be used for timing purposes for devices such as a "fuse" timer for delayed activation of a device/function (e.g., weapons systems) or as an "odometer" that monitors a total run-time (or a total time since a first use) of a device/system. The "odometer"-type timer can similarly be used to monitor elapsed time between service/maintenance of a device or system. The electrodeposit is persistent in that the state of the timer (i.e., the length of the electrodeposit growth) is preserved if power is removed from the system and/or the timing device. Therefore, the timing function of the timing device of FIG. 1 is non-volatile.

Although the example of FIG. 1 and various other examples provided herein discuss regulating a rate of growth of the electrodeposit 108 by controlling the magnitude and duty cycle of an applied current, in some implementations, other mechanisms can be implemented to control the applied current and, thereby, regulate the rate of electrodeposit growth. For example, in some implementations, the current may be an exponential function of voltage and, therefore, the magnitude of the driving voltage can be adjusted/controlled to define or regulate the growth rate of the electrodeposit 108 and the timing interval of the timing device 100.

A monitoring circuit or controller 109 is configured to monitor an electrical characteristic of the timing device 100 that is indicative of the time-dependent growth of the electrodeposit and is, thereby, indicative of an elapsed timer duration. In the particular example of FIG. 1, the monitoring circuit/controller 109 monitors a resistance between the cathode 101 and the anode 103. Because the electrodeposit 108 is a conductive material and the electrolyte is of a relatively high resistance, the measurable resistance between the cathode 101 and the anode 103 decreases as the growth of the electrodeposit 108 approaches the anode 103. Furthermore, the monitoring circuit/controller 109 can be integrated as part of the timing device 100 or can be provided as a separate component (e.g., a separate microcontroller) that is coupled to the cathode 101 and the anode 103 through a pair of electrical contacts 111 and 113, respectively.

Although the example of FIG. 1 monitors a resistance, other implementations may be designed and configured to monitor other electrical characteristics of the timing device that are indicative of growth of the electrodeposit between the cathode 101 and the anode 103 instead of or in addition to monitoring resistance. For example, as discussed in further detail below, in some implementations, the timing device is configured to monitor a capacitance that is indicative of a degree of growth of the electrodeposit.

The electrolyte allows for the transport of metal ions and the subsequent immobilization of these ions via reduction by electrons supplied by a negatively charged electrode (i.e., a cathode 101). In the example of FIG. 1, the cathode 101 is constructed of a relatively inert material and, as such, the cathode 101 will not supply ions into the reaction environment—only electrons. The anode 103 is constructed of the same metal as in the electrolyte (e.g., Ag, Cu, etc.). The anode 103 is oxidized to allow ions to flow into an ion conductor to replace those (and the charge they carry) that are removed by reduction. In the case of a metal M (e.g., Ag, Cu, and the like) with oxidation state z (1, 2), the redox reactions at both the electrodes are:

Anode: $M \rightarrow M^{z+} + ze^-$

Cathode: $M^{z+} + ze^- \rightarrow M$.

The metal cations (e.g., $M^{z+}$) diffuse down the concentration gradient created by their removal via reduction at the cathode 101 and will also drift in the direction of the applied field (i.e., toward the cathode 101). At the cathode 101, nucleation kinetics dictate that a potential difference must be overcome for electrodeposition to proceed. The potential difference is relatively small (e.g., in the order of a few tenths of a volt). Although, it should be noted that a larger bias (e.g., a few volts) may be necessary to overcome series resistances in some implementations. During the initial stages of electrodeposit formation (i.e., nucleation) electrons for the reduction of the ions are supplied directly from the cathode 101. However, as growth proceeds, the emergent conductive deposit (i.e., electrodeposit 108) supplies the electrons so the ions can become reduced and immobilized on the electrodeposit 108 itself.

The electrons (e.g., $e^-$) flow in an external circuit with the current source 107 to provide the necessary voltage to drive the process. If the electrons are supplied by a constant current source 107 and assuming that the electrolyte is a poor conductor of electrons (to reduce the flow of current that doesn't result in electrodeposition), the rate of electrodeposition and the consequent rate of the elongation of the electrodeposit will be constant.

In some implementations, copper is used as the anode material and is included in the electrolyte. Copper is commonly used in integrated circuit fabrication and each $m^3$ of Cu contains $8.46 \times 10^{28}$ atoms (or 84.6 atoms per $nm^3$). Each $Cu^{2+}$ ion requires two electrons from the external circuit to become reduced to form a deposited atom so each $nm^3$ of Cu will require 84.6 times the charge on each electron ($1.60 \times 10^{-19}$ C$\times 2$) which is $2.71 \times 10^{-17}$ C of Faradaic charge. This charge is the integral of the current over time and so a current of 100 nA applied over a period of 10 ns with would supply sufficient charge ($10^{-15}$ C) to deposit 36.9 $nm^3$ of Cu. If the tip of the electrodeposit is in the order of 5 nm thick and 20 nm wide (i.e., cross-sectional area $A_m=100$ $nm^2$), and the copper is deposited evenly over this surface, this pulse would deposit 0.369 nm or approximately one monolayer of Cu.

As discussed above, the timing device of FIG. 1 includes a solid electrolyte channel 105. In various embodiments, this channel is of various different lengths and of minimal width to confine and direct the formation of the electrodeposit between the two electrodes (i.e., the cathode 101 and the anode 103). The starting or "off" resistance (e.g., $R_{off}$) of the channel can be described as a geometric function of the channel dimensions, following $R_{off}=\rho_e L_e/dW_c$, where $\rho_e$ is the resistivity of the electrolyte layer (the minimum being in the order of $10^3$ Ω·cm for a high mobility chalcogenide glass electrolyte), d the thickness of the electrolyte layer, and $W_e$ and $L_e$ the width and length, respectively, of the electrolyte layer. For example, a 20 nm×10 μm ($W_e \times L_e$) device with a 20 nm thick electrolyte will therefore have an $R_{off}$ of at least 250 GΩ. This resistivity would be orders of magnitude higher for oxide-based ion conductors which have a much higher resistivity.

Figure 2:
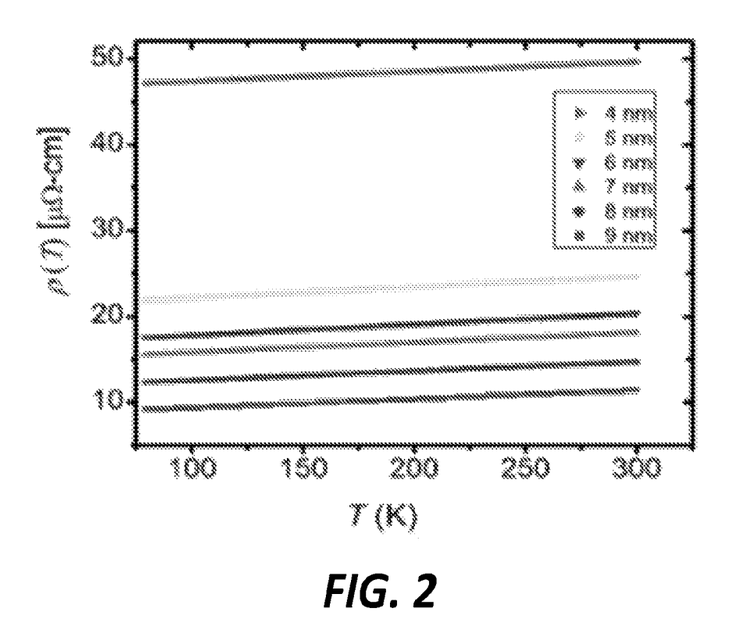
FIG. 2 is a graph of the resistivity of Cu films relative to the thickness of the Cu films.
Figure 3:
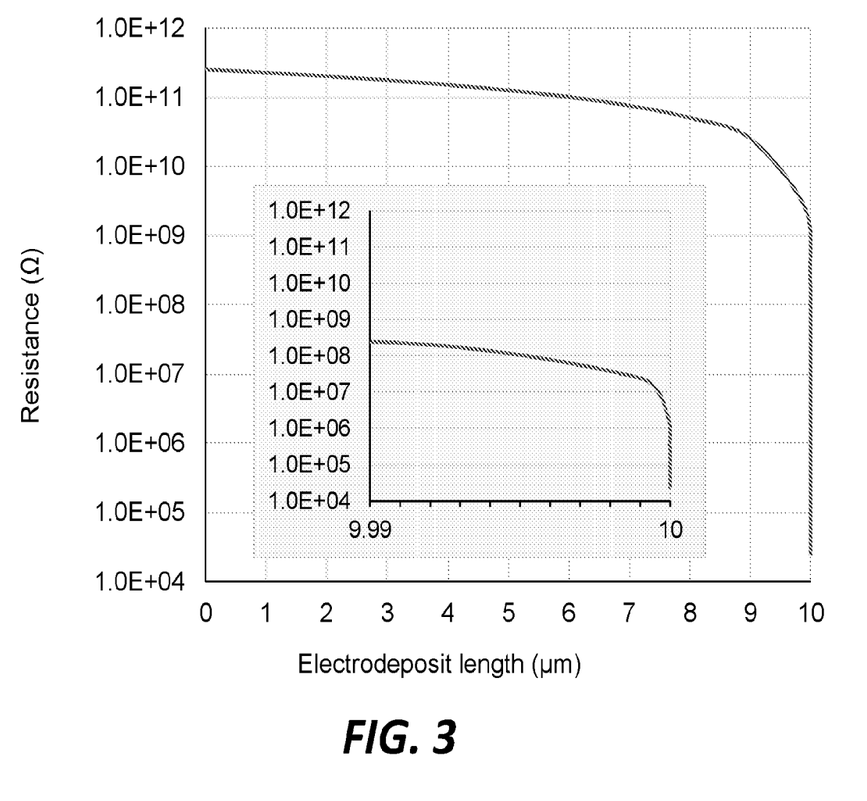
FIG. 3 is a graph of the resistance between the cathode and the anode of the timing device of FIG. 1 as a function of the length of the electrodeposit.

The resistance (e.g., $R_m$) of the metal electrodeposit 108 is given by $R_m=\rho_m L_m/A_m$, where $\rho_m$ is the resistivity of the metal, and $L_m$ and $A_m$ are the length and cross-sectional area, respectively, of the metal electrodeposit. For example, the bulk resistivity of Cu is 1.7 µΩ·cm but for thin films, $\rho_m$ will depend on the thickness of the Cu conductor due to surface scattering. As illustrated in the graph of FIG. 2, the resistivity of a 5 nm thick Cu film is in the order of 25µΩ·cm at room temperature. If the electrodeposit had a cross-sectional area of, for example, 100 nm² (5 nm×20 nm), the resistance of the electrodeposit would be in the order of 2.5 kΩ/µm of length. If the electrodeposit had to bridge the 10 µm long channel above, the final resistance of the electrodeposit would be 25 kΩ, some seven orders of magnitude lower than the starting resistance. Since the resistance of the structure between the electrodes is dominated by the high resistivity of the electrolyte until the point when the highly conductive electrodeposit almost shorts the electrodes together, a dramatic reduction in resistance occurs quite suddenly, as shown in FIG. 3.

Figure 4:
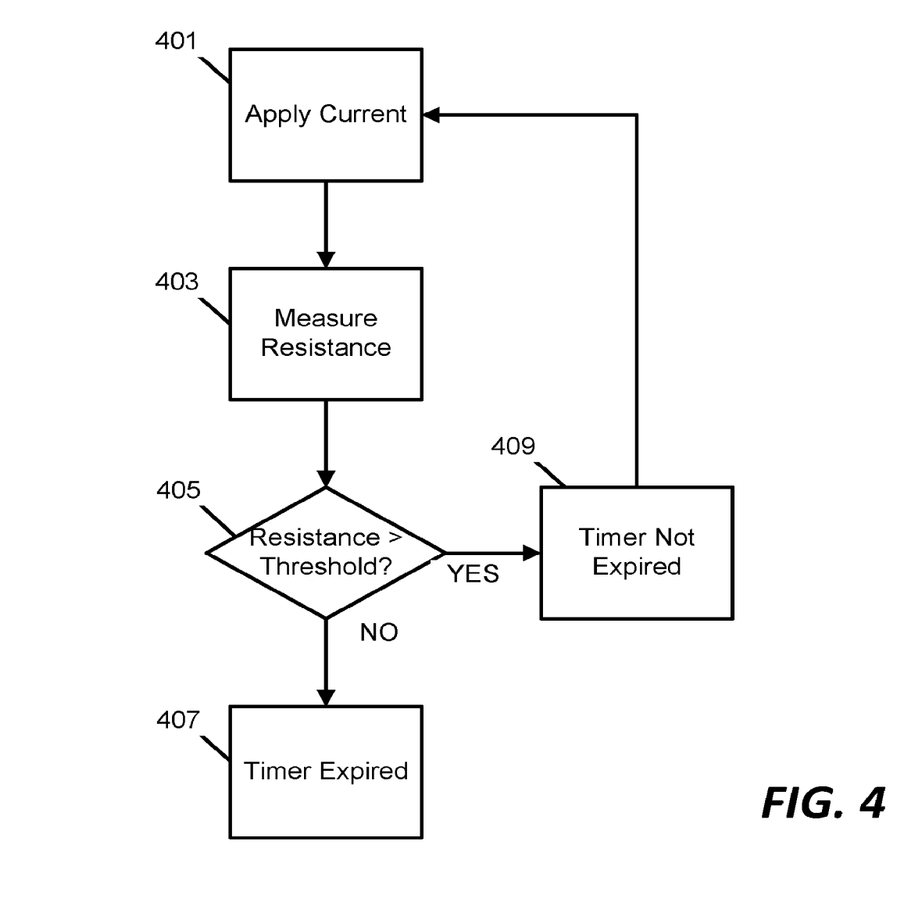
FIG. 4 is a flowchart of a method for operating the timing device of FIG. 1 to detect expiration of a timer duration.

This large and sudden change in resistance combined with a controllable growth rate of the electrodeposit 108, which is governed by an adjustable or constant current source 107, leads to timing functionality. FIG. 4 illustrates one example of a method for operating the timing device 100 using resistance as the measurable electrical characteristic that is monitored. A current is applied by the current source 107 (block 401) and a resistance between the anode 103 and the cathode 101 is measured by the monitoring circuit/controller 109 (block 403). If the resistance is greater than a defined threshold (block 405), then the electrodeposit 108 has not reached the requisite degree of growth and, accordingly, the timer has not yet expired (block 409). However, once the measured resistance does exceed the threshold (block 405), the electrodeposit 108 has reached the requisite degree of growth and, therefore, the monitoring circuit/controller 109 determines that the timer has expired (block 407).

Figure 5A:
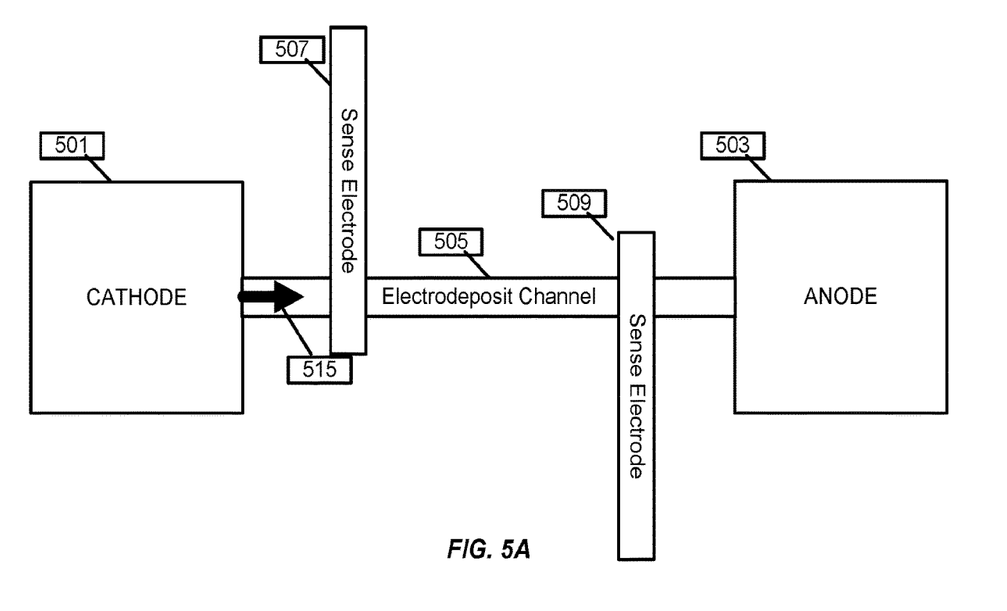
FIG. 5A is a schematic diagram of a timing device with additional sense electrodes positioned between the anode and the cathode according to another embodiment.
Figure 5B:
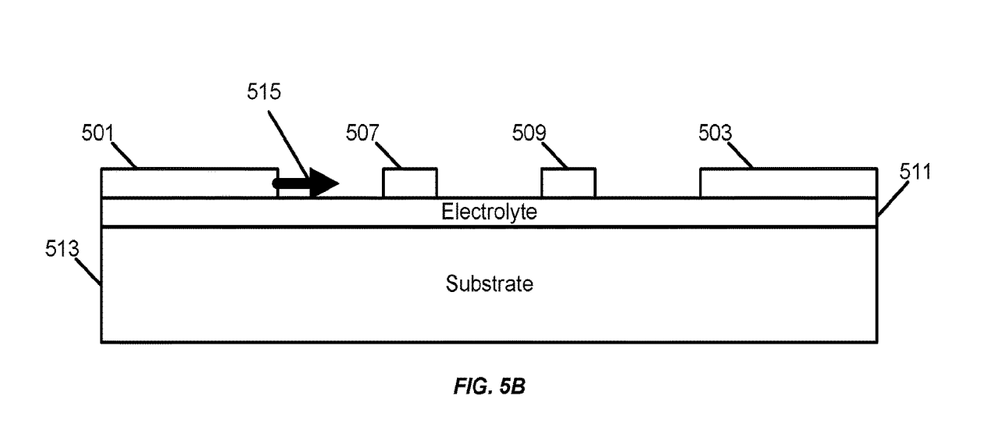
FIG. 5B is a cross-sectional view of the timing device of FIG. 5A configured for electrodeposit growth from the cathode towards the anode.

The examples discussed above measure only a single electrical characteristic (i.e., resistance between an anode 103 and a cathode 101) to determine expiration of a single timer duration. However, other implementation may be configured to monitor additional electrical characteristics and to determine expiration of multiple different timer durations. FIGS. 5A and 5B illustrates an example of one such implementation that again includes a cathode 501 and an anode 503 separated by an electrolyte channel 505. However, unlike the example of FIG. 1, two additional sense electrodes 507, 509 are positioned between the anode 503 and the cathode 501 in contact with the electrolyte 511 within the channel 505 above the substrate 513. The additional sense electrodes 507, 509 facilitate measurement of resistance of portions of the electrodeposit 515. As in the example of FIG. 1, the electrodeposit 515 frows outward from the cathode 501 until it contacts the first sense electrode 507, making sense electrode 507 the "new cathode." The growth of the electrodeposit 515 continues until it contacts the second sense electrode 509 (making it the new cathode) and ultimately until it contacts the anode 503.

This arrangement offers additional operational flexibility in that multiple timing intervals may be incorporated in a single device. The timing intervals will depend on the placement of the sensing electrodes and which electrodes are used for resistance measurement. For example, the resistance changes can be measured between the cathode 501 and the first sense electrode 507, between the cathode 501 and the second sense electrode 509, between the cathode 501 and the anode 503, between the first sense electrode 507 and the second sense electrode 509, and/or between the second sense electrode 509 and the anode. Certain circuit functions may be triggered as the electrodeposit 515 contacts the various electrodes.

Figure 6:
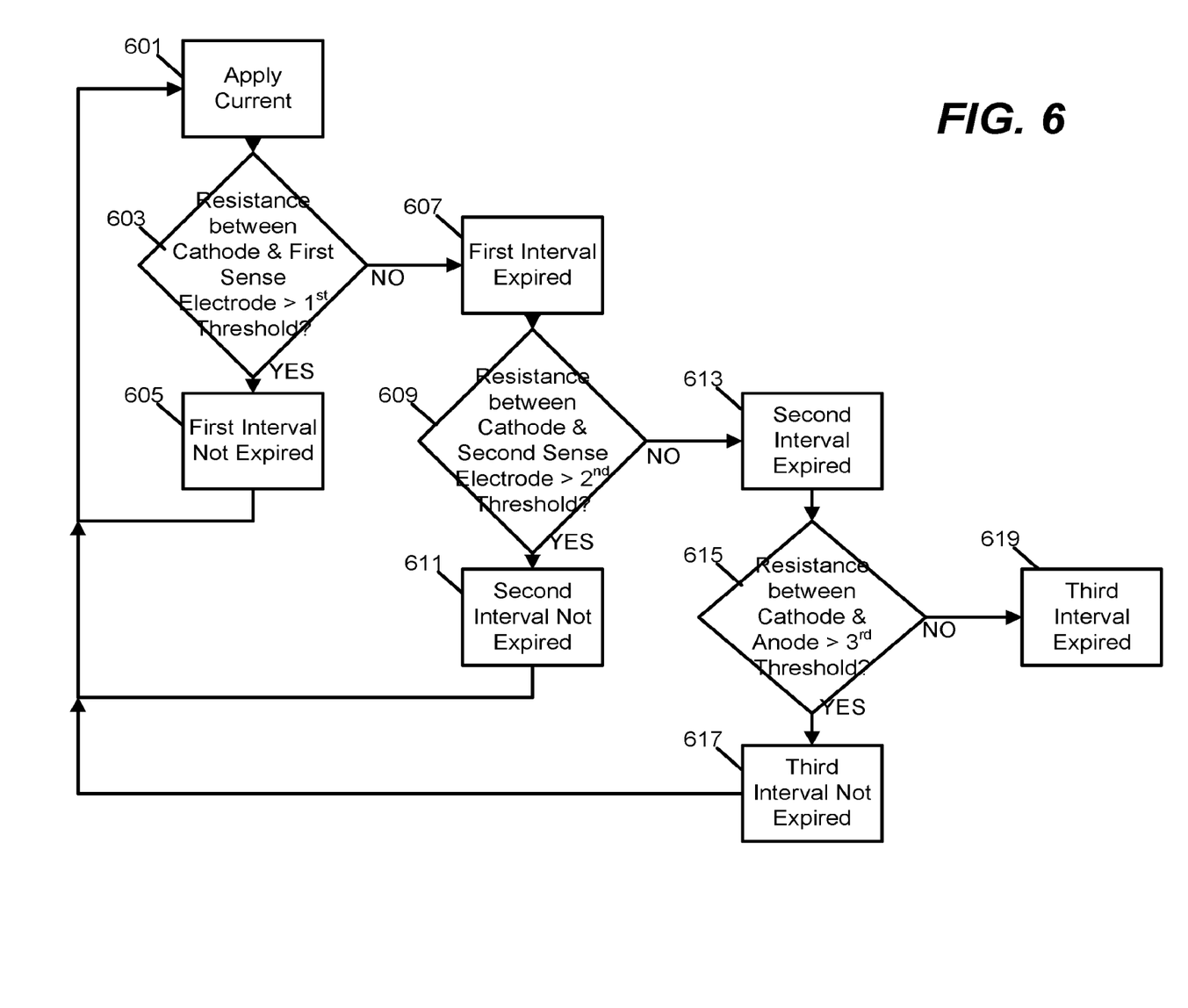
FIG. 6 is a flowchart of a method for operating the timing device of FIGS. 5A and 5B to detect expiration of multiple different timer durations.

FIG. 6 illustrates an example of one method of monitoring resistances between various electrode pairs in the timing device of FIGS. 5A and 5B to detect expiration of each of a plurality of different timer durations. A current is applied between the anode 503 and the cathode 501 (block 601). If the resistance measured between the cathode 501 and the first sense electrode 507 exceeds a first threshold (block 603), then the first timer interval has not yet expired (block 605). However, if the resistance falls below the first threshold, then the growth of the electrodeposit 515 indicates that the first timer interval is expired (block 607).

Similarly, the resistance between the cathode 501 and the second sense electrode 509 is measured and compared to a second resistance threshold (block 609). If this measured resistance exceeds the second threshold, then the second timer interval has not yet expired (block 611)—if not, the growth of the electrodeposit 515 has reached a degree indicative of expiration of the second timer interval (block 613). Finally, the resistance between the cathode 501 and the anode 503 is measured and compared to a third resistance threshold (block 615). If this measured resistance exceeds the third resistance threshold, then the third timer interval has not yet expired (block 617)—if not, then the growth of the electrodeposit 515 has reached a degree indicative of expiration of the third timer interval (block 619).

As discussed above, the rate of growth of the electrodeposit can be controlled by adjusting the amplitude and the duty cycle of a current applied to the timer device. Therefore, the duration of each of the three timer intervals discussed in the example of FIG. 6 can be defined based the applied current and spacing between each of the electrodes.

In some implementations, the limit of the number of additional sense electrodes that can be used along a single electrolyte channel 505 may depend on the length of the channel and the lithographic capabilities of the process. For example, if the process half-pitch capability is 25 nm, the timing device can accommodate some 20 sensing electrodes per µm of channel length, which can lead to a large number of possible electrode pair combinations for a timing device that was several µm in total length.

Additionally, a low electron conductivity electrolyte, such as an oxide-based material, may be employed in the multielectrode scheme (e.g., as illustrated in FIGS. 5A and 5B) to prevent electron flow in the electrolyte from allowing ion reduction and growth to occur at the sense electrodes even before the (electron supplying) electrodeposit arrives at these electrodes to make them the new cathodes. However, in other implementations, the additional sensing electrodes are also biased during growth so that simultaneous electrodeposition occurs between sets of electrodes.

Figure 7:
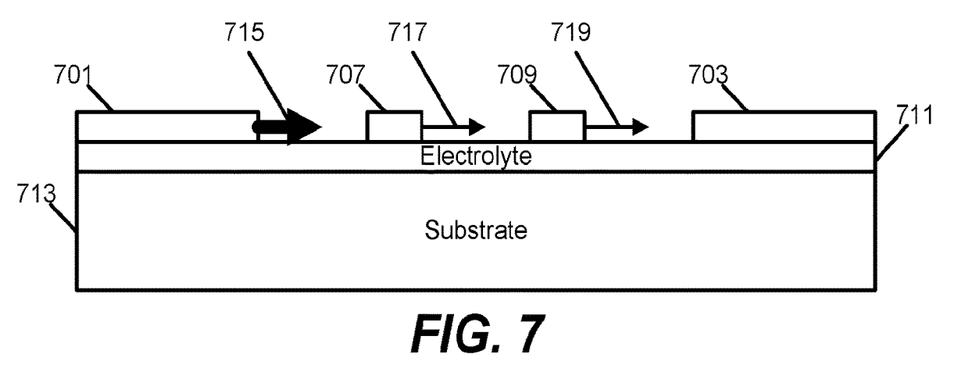
FIG. 7 is a cross-sectional view of an alternative embodiment of the timing device of FIG. 5A configured from elecrodeposit growth from the cathode and from each of the additional sense electrodes towards the anode.

FIG. 7 illustrates an example of a timing device that includes a cathode 701, an anode 703, a first sense electrode 707, and a second sense electrode 709 all arranged in contact with an electrolyte layer 711 positioned on a substrate 713. In this example, the cathode 701, the first sense electrode 707, and the second sense electrode 709 are all biased to act as "cathodes" with the anode 703 serving as a common "anode." In this configuration, electrodeposits 715, 717, 719 develop towards the anode 703 from each of the electrodes 701, 707, 709, respectively, at the same time such that the electrodeposits 717, 719 extending from the first sense electrode 707 and the second sense electrode 709, respectively, begin to form even before the electrodeposit 715 extending from the cathode 701 reaches the first sense electrode 707. The growth rate in each segment can be adjusted based on the bias applied to each electrode which, in turn, will determine the current flow in each segment.

The implementation illustrated in FIG. 7 provides operational flexibility and multiple timing intervals as well as implementing logic functions based on which electrodes are biased. For example, the electrodes can be configured to operate as multiple "switches" in a single device structure. If the resistance between electrodes 701 and 703 represents an output of the logic device (high=0, low=1), then the state of electrodeposit growth in each segment (i.e., between electrodes 701 and 707, between electrodes 707 and 709, and between electrodes 709 and 703) would have to reach the respective low resistance state before the output of the device as a whole would be in its low resistance state. Because the bridging of these segments by growth of the respective electrodeposit depends on the bias/current applied for a particular time to electrodes 701, 707, and 709, the bias/current applied to each electrode functions as the inputs to the logic element. This resulting functionality might be described as similar to a three input AND gate; however, unlike a conventional AND gate, the output of the logic device is "true" (i.e., binary high), when all three timing segments had sufficient time at bias for the electrodeposit growth to reach a low resistance state. Furthermore, because the inputs to the logic element are time durations rather than mere voltage levels, this logic element has utility in complex timing functions where multiple timers are involved or when a full consensus of multiple timers is necessary to trigger a binary high output of the logic device.

Although the examples described above monitor resistance between electrodes as indicative of time-dependent electrodeposit growth, other measurable electrical characteristics such as, for example, capacitance may be utilized in other implementations. However, if the timing device structure includes a 10 μm long channel, the cross-sectional area at the growth front of the electrodeposit is approximately 100 nm$^2$ and the "lateral" capacitance between the cross-sectional area at the growth front of the electrodeposit and the opposite electrode (e.g., 100 nm$^2$), it is in the order of $10^{-22}$ F at the start of growth and is still only around $10^{-19}$ F when the growth front is within 10 nm of the electrode. Such low capacitance can be difficult to measure.

Figure 8:
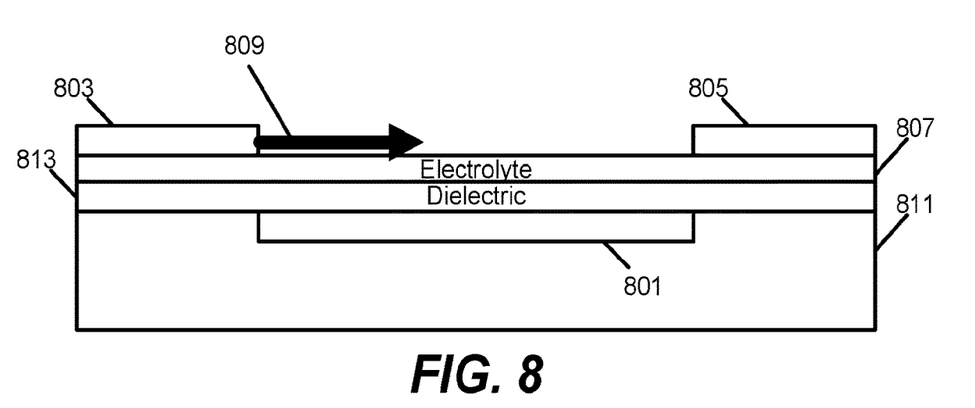
FIG. 8 is a cross-sectional view of a timing device configured to monitor expiration of a timer duration based on a capacitance between a sense electrode and a growing electrodeposit.

FIG. 8 illustrates an example of a timing device that uses a sense electrode 801 positioned in parallel with the main dendrite growth direction to generate a larger capacitance between the electrodeposit growth and the sense electrode 801. The timing device includes a cathode 803 and an anode 805 both in contact with an electrolyte layer. Again, an electrodeposit 809 forms on the cathode 803 extending towards the anode 805 as a current is applied between the cathode 803 and the anode 805. However, in the example of FIG. 8, the sense electrode 801 is positioned between the electrolyte layer 807 and the substrate 811 so that the forming electrodeposit 809 does not contact the sense electrode 801. In some embodiments, the timing device also includes a dielectric layer 813 to further separate the sense electrode 801 from the electrolyte 807 and the electrodeposit 809.

As the electrodeposit 809 grows outward from the cathode 803, the capacitance between the electrodeposit 809 and the underlying sensing electrode 801 increases. For a 10 nm thick chalcogenide-based solid electrolyte 807 with a dielectric constant of 70, a 10 nm thick silicon nitride dielectric 813 with a dielectric constant of 7.5, and a 20 nm wide electrodeposit 809, the capacitance between the electrodeposit 809 and the sense electrode 801 will be in the order of $10^{-16}$ F/μm. This is considerably larger than the lateral capacitance between the growth front of the electrodeposit 809 and the anode 805. Furthermore, even in a narrow channel, the electrodeposit morphology is dendritic and, accordingly, the effective width of the "top plate" of the capacitor will be much larger than the width of a single branch of the electrodeposit 809. Therefore, if an electrodeposit 809 has a 1 μm effective width, the capacitance, for the example above, rises to $6\times10^{-15}$ F/μm—a capacitance that is similar to that of DRAM structures and that can be sensed relatively easily. In some timing device implementations, a difference between an initial capacitance and a final capacitance is monitored. The initial capacitance is governed by fringing effects between the cathode 803 and the sense electrode 801 (which can be made considerably less than $10^{-15}$ F). The final capacitance for a 10 μm long structure will be closer to $6\times10^{-14}$ F—a difference that can be detected using a sense amplifier.

Figure 9:
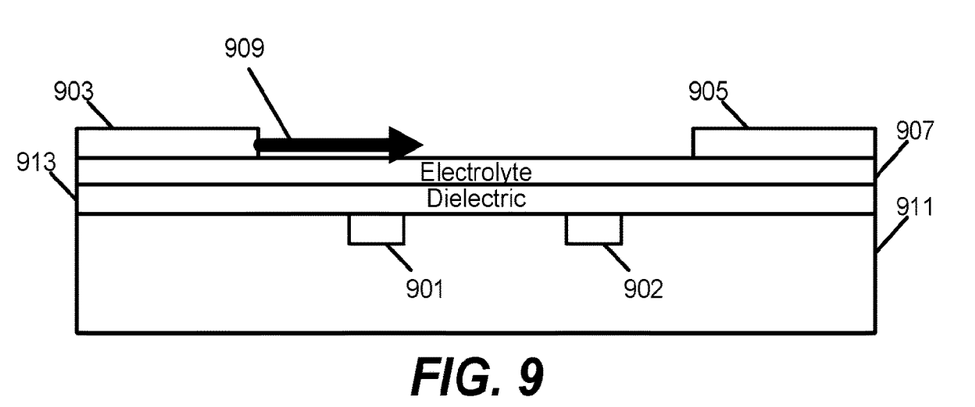
FIG. 9 is a cross-sectional view of another timing device configured to monitor expiration of multiple different timer durations based on a capacitance between a growing electrodeposit and two separate sense electrodes.

In other implementations, a capacitance-based timing device can include more than one sense electrodes that cross the growth direction of the electrodeposit to create a series of discrete capacitors as the electrodeposit grows over them. FIG. 9 illustrates an example of one such timing device that includes a first sense electrode 901 and a second sense electrode 902. Like in the example of FIG. 8, the timing device of FIG. 9 also includes a cathode 903 and an anode 905 both in contact with an electrolyte 907 such that an electrodeposit 909 forms on the cathode 903 extending towards the anode 905 as a current is applied between the cathode 903 and the anode 905. The two sense electrodes 901, 902 are positioned at different locations parallel to the direction of growth of the electrodeposit 909 and are located between the electrolyte layer 907 and the substrate 911. In some implementations, a dielectric layer 913 is also positioned between the electrolyte 907 and the sense electrodes 901, 902.

In the example of FIG. 9, a 1 μm wide sensing electrodes and a 1 μm wide electrodeposit would provide capacitances between the cathode 903 and the first sense electrode 901 that rises from essentially zero (at the beginning of electrodeposit formation) to approximately $6\times10^{-15}$ F. Similarly, as growth of the electrodeposit 909 proceeds, the capacitance between the cathode 903 and the second sense electrode 902 will also rise. This multiple-sense electrode configuration provides similar operational flexibility as the multi-electrode resistive method described above in reference to FIGS. 5A and 5B, including multiple timing intervals in the same device as illustrated in the flowchart of FIG. 6. Furthermore, if the sense electrodes 901, 902 are connected together, the measured capacitance will rise in discrete increments of $6\times10^{-15}$ F as the electrodeposit grows over each electrode, allowing a discretization of the output. This functionality can be utilized to provide a "countdown" function or to determine the position of the electrodeposit growth in the channel with an accuracy that increases based on the spacing of the sense electrodes.

As discussed above in reference to FIG. 1, the timing device utilizing time-dependent, current-controlled electrodeposit growth can be coupled to a monitoring circuit or to a controller. Similarly, the timing device can be used to monitor operation and, for example, to track a total "run time" of an electronic device. The timing device can be used in at least three connected configurations. First, the timing device can be provided as a separate "dielet" that contains the timing device and support circuitry and that is physically connected to a chip that is being monitored by the timing device. The dielet could be provided within a package well along with the chip or could be mounted on a carrier or board that also contains the packaged chip. Second, the timing device could be provided as a part of the package itself (e.g., formed on a package lid) and physically connected to the monitored chip. Third, the timing device could be fully integrated with the monitored chip in a back-end-of-line (BEOL) process performed in the same manufacturing facility as the chip or in a separate BEOL post-processing facility.

Figure 10A:
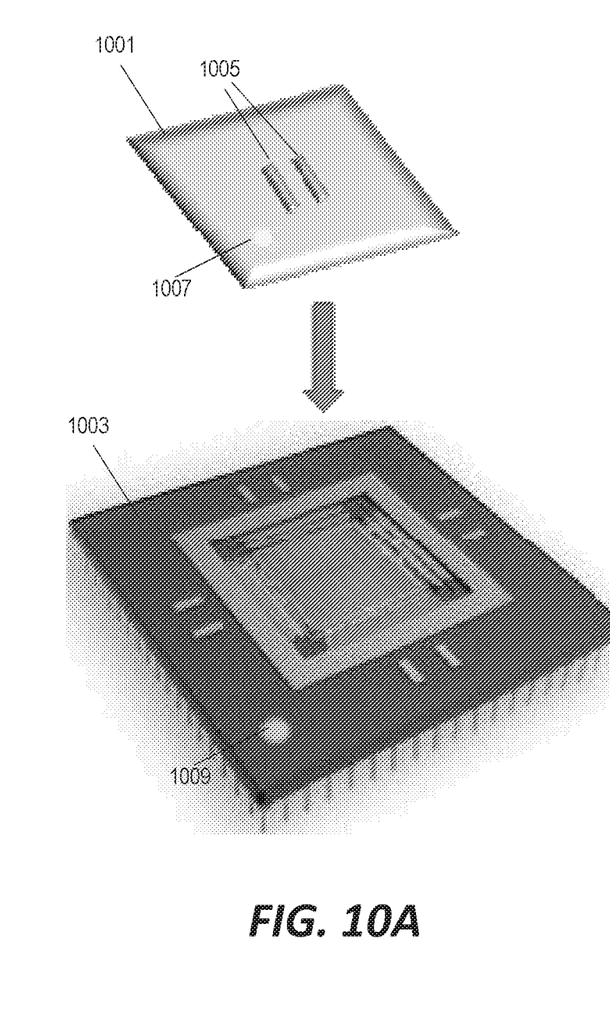
FIG. 10A is a perspective view of an electronic device package with a timing device incorporated into the package cover.
Figure 10B:
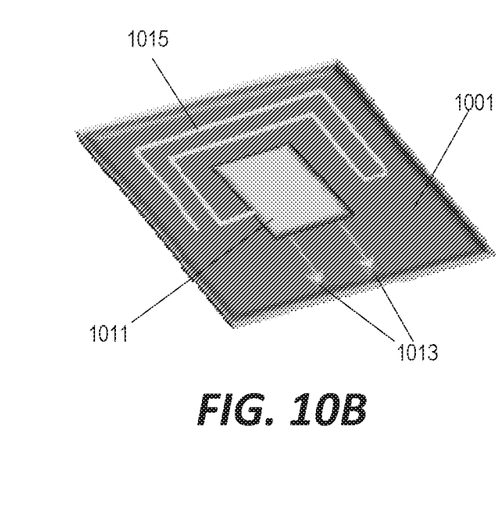
FIG. 10B is a perspective view of the underside of the package cover from the electronic device package of FIG. 10A.

However, in some applications—for example, where chips have been inspected/certified and cannot be altered—physical connection between the chip and the timing device may not be permitted. FIGS. 10A and 10B illustrate an example of a timing device used to monitor an integrated circuit chip without a physical connection between the chip and the timing device. A package lid 1001 is coupleable to a chip package 1003. The exterior surface of the package lid 1001 (as shown in FIG. 10A) includes a pair of interrogator contacts 1005 through which an electrical characteristic indicative of growth of the electrodeposit in the timing device (e.g., resistance or capacitance) can be monitored. A matched pair of trust marks is employed on the lid (trust mark 1007) and on the package (trust mark 1009) to prevent unauthorized removal or reuse of the timing circuit. In some implementations, these trust marks 1007, 1009 include dendritic identifiers.

As shown in FIG. 10B, the underside of the package lid 1001 includes the timing device 1011, a pair of contacts 1013, and an antenna 1015. The antenna 1015 is connected to the timing device 1011 and picks up the electromagnetic radiation emitted by the clock of a chip operating on the package 1003. This electromagnetic radiation is used to drive the timing function of the timing device 1011 to monitor a total run-time of the chip on operating on the package 1003. The power for the timing device 1011 is fed from the package (Vdd and GND) through the contacts 1013 (e.g., spring pins) or is scavenged using an RF coil built into the lid 1001. The state of the electrodeposit growth in the timing device 1011 is monitored/interrogated in the assembled package through the contacts 1005 on the external surface of the lid 1001 or through an RF coil.

In the examples described above, the duration between timer events, such as a predetermined resistance or capacitance change, depends on how fast the electrodeposit grows and how far it has to grow. Growth rate is controlled by the current supplied, which is a function of the operation of the device, and the spacing of the electrodes, which would be set during the design of the device structure. For example, a "short fuse" timing device would involve a fast growth rate between closely-spaced electrodes while a "chip odometer" (such as illustrated in the example of FIGS. 10A and 10B) might use a relatively slow growth between multiple relatively widely-spaced electrodes so that the timer could measure runtimes extending to tens of years. In one prior example, the electrodeposit had a growth rate of 0.369 nm in 10 ns or 3.69 cm/s. Even if the current is decreased by several orders of magnitude, this growth rate may still be too high for certain long-term timing applications.

To extend the duration of the timer, the length of the channel could be extended linearly or can be arranged in an alternating "switchback" pattern. However, this may be somewhat impractical in certain implementations. Alternatively (or additionally), the length of the duration of the timer is extended in some implementations by supplying discrete amounts of charge to the timing device via current pulses. These pulses can be regulated, for example, by a current source such as illustrated in the example of FIG. 1 or using the clock of a digital circuit device that is being monitored by the timing device. If, for example, a 100 nA current is supplied in 10 ns pulse intervals and the distance between the electrodes is 10 μm, it would require 27,100 such pulses for the electrodeposit to fully bridge the channel. If the pulses are regulated so that the pulses are applied with a set interval between each pulse, the total time can be altered to achieve a particular device event via bridging growth as shown in Table 1. This "pulsed" electrodeposit growth is made possible because due to the persistence of the electrodeposit even when power is removed from the timing device (e.g., between current pulses).

TABLE 1

| | Pulse interval | | | | | |
|---|---|---|---|---|---|---|
| | 37 μs | 2.2 ms | 0.13 s | 3.2 s | 100 s | 1100 s |
| Time to event Approx. duration | 1.00 Second | 59.6 Minute | 3,520 Hour | 86,720 Day | 2,710,000 Month | 27,800,000 Year |

Considering the monitoring of integrated circuits, since the timing device can be supplied with pulses from any part of a circuit and not just from the system clock, it is also possible to use the technology to determine how long (or how often) individual circuit blocks have been operated (or accessed). The device is simple, compact, and can be integrated above the CMOS circuitry, as illustrated in the example of FIGS. 10A and 10B, so that every significant circuit block can have its own run timer.

Another timing mode that can be utilized which is related to the non-volatility of the device state is system/device off time. Because the electrodeposit growth stops and its length is preserved when the current is removed, the difference between "real time" and "device time" as indicated by the timing circuit can be used to determine how long the system or component has been "down." This could have significant utility in maintenance or anti-tampering operations.

Because the electrodeposit is persistent and does not spontaneously dissolve when the bias is removed, the timer does not reset when the power is removed from the system. However, in some implementations, it is possible to deliberately reverse the growth by reversing the bias to oxidize the metal in the electrodeposit and thereby dissolve it. In one example, both the anode and the cathode are made from the "active" metal contained within the electrolyte (and the electrodeposit) and reversal of the bias (e.g, the direction of the current) causes the growth of the electrodeposit from the opposite electrode. Accordingly, growth of the electrodeposit can be selectively initiated from either electrodes (for example, the electrode identified as the anode 103 and the cathode 101 in FIG. 1).

In some implementations, if growth has already been initiated from one electrode, reversing the bias will dissolve the existing electrodeposit while a new electrodeposit grows from the opposite electrode concurrently. This leads to additional timing functionality as the new electrodeposit could be detected by the sensing electrodes in opposite order (e.g., contacting/covering electrode 509 before electrode 507 in the example of FIGS. 5A and 5B). Also, because growth in the reverse direction is itself an indication of timer reversal, which could be deliberate or unauthorized, this could be used in some implementations to detect tampering. Circuitry, such as a diode in series with the growth supply, could also be incorporated to prevent bias reversal in certain implementations where timer reversal is never required.

In some implementations, an asymmetric electrode arrangement can be employed to reset the timing device without reverse growth. The anode would contain the active metal as in the examples above, but the cathode and sensing electrodes would be made from an electrochemically inert conductor. This would prevent ion current flow in the opposite direction during reverse bias (other than that caused by the oxidation of an already formed electrodeposit) and thereby reduces the possibility of electrodeposit growth in the opposite direction. In such implementations, the electrodeposit can be controllably shortened to partially reset the timer or to return the timer to close to its original starting state.

As noted above, in some implementations, a serpentine channel layout is used to extend the total length of the channel and, thereby, extend the duration of the timer. Serpentine layouts may be used to embed very long channels in small areas, as the electrodeposit described above will grow around corners and hairpin turns. In addition to having a set length or lengths between electrodes to set timing interval(s), the width of the channel can also be adjusted as a design factor. In some implementations, the channel could be fabricated to a minimum width attainable via lithography to minimize the width/spread of the dendrite. Alternatively, the channel could be configured to be wide enough to allow the dendritic electrodeposit growth to spread out and to produce a larger effective area, which would, for example, improve the measurable changes in capacitance as the electrodeposit continues to grow. In some implementations, the channel is formed by a physical indentation or groove in the solid electrolyte itself as the electrodeposition described above tends to occur along such topographical features.

The device may be fabricated with few layers of inexpensive materials and without need for critical/minimum-geometry lithography. The device may be placed at the back-end-of-line (BEOL), being fabricated along with the final layers of interconnect and passivation. The solid electrolyte is formed by adding the active metal (e.g., Cu) into a host glass by a variety of means, including thermal diffusion, photo-dissolution, co-deposition, and the like. The host glass may be an oxide such as $SiO_2$ or $WO_3$, or a higher chalcogenide such as $GeSe_2$ or $GeS_2$. As mentioned previously, the anode may be the same metal as in the electrolyte and the cathode and sensing electrodes may be formed of the same metal or of a conductor that is essentially electrochemically inert, (e.g., W, WN, or TiN).

Some implementations that monitor growth of the electrodeposit using measurable resistance include a single layer of patterned electrolyte and a single patterned layer of electrodes (e.g., growth electrodes and sensing electrodes). The construction of some implementations that monitor capacitance-change is somewhat more complicated in that the sensing electrodes have to be separated from the electrodeposit and will be formed in a separate layer of metallization from the growth electrodes (cathode/anode). An additional layer of dielectric may also be necessary as described in the examples of FIGS. 8 and 9, depending on the insulating properties of the electrolyte. This dielectric could be deposited oxide ($SiO_2$), nitride ($Si_3N_4$), or polymer (polyimide).

In some implementations, the electrolyte is covered in a layer of passivation to protect its surface and the electrodeposit once grown. The electrodeposit will still grow under a variety of materials including thin films of relatively hard substances such as $SiO_2$ and thick films of pliable material such as parylene.

Timing devices, such as those described above, operate at low voltage and low current and can be readily integrated into a low power system or circuit. The construction of the timing device includes only a few layers and no expensive materials. The timing device uses materials that are compatible with integrated circuit manufacture and can be fabricated in the back-end-of-line (BEOL) without signification additional CMOS circuitry. Due to the persistence of the electrodeposit, the timing device retains state even when the system power is removed and, in some implementations, is resettable with application of reverse bias. Finally, because the materials and growth processes are not affected by radiation, some implementations of the timing device can be used in military, nuclear, or medical applications.

Thus, the invention provides, among other things, a timing device in which a measurable electrical characteristic is indicative of a time-dependent growth of an electrodeposit. Various features and advantages of the invention are set forth in the following claims.

What is claimed is:

1. A timing device comprising:
   a first electrode;
   a second electrode;
   an electrolyte positioned between the first electrode and the second electrode, the electrolyte including a material selected such that an electrodeposit forms on the first electrode when a current is applied between the first electrode and the second electrode,
   wherein a measureable electrical characteristic of the timing device is indicative of a time-dependent degree of growth of the electrodeposit between the first electrode and the second electrode,
   wherein a resistivity of the electrolyte is higher than a resistivity of the electrodeposit, and wherein the measurable electrical characteristic indicative of the time-dependent degree of growth of the electrodeposit includes a resistance between the first electrode and the second electrode; and
   a controller configured to detect expiration of a timing interval when the monitored resistance between the first electrode and the second electrode falls below a resistance threshold.

2. The timing device of claim 1, wherein the second electrode includes an anode formed of a first metal, and wherein the electrolyte includes the same first metal as the anode.

3. The timing device of claim 2, wherein the first electrode includes a cathode formed of an inert material, and wherein, in response to the applied current, electrons pass from the cathode to the anode through the electrolyte and metal ions pass from the anode to the cathode through the electrolyte to form the electrodeposit on the cathode.

4. The timing device of claim 2, wherein the first metal of the anode includes copper, and wherein the electrolyte includes a glass electrolyte.

5. The timing device of claim 1, further comprising a sense electrode positioned in contact with the electrolyte between the first electrode and the second electrode.

6. The timing device of claim 1, further comprising a sense electrode positioned proximal to the electrolyte between the first electrode and the second electrode such that the formation of the electrodeposit will not contact the sense electrode, and wherein the measurable electrical characteristic indicative of the time-dependent degree of growth of the electrodeposit includes a capacitance between the first electrode and the sense electrode.

7. The timing device of claim 6, wherein the electrolyte is positioned such that the electrodeposit forms on the first electrode along a first surface of the electrolyte and wherein the sense electrode is positioned to contact the electrolyte at a location other than the first surface of the electrolyte.

8. The timing device of claim 6, further comprising a dielectric layer positioned between the sense electrode and the electrolyte.

9. The timing device of claim 1, further comprising a current source configured to apply the current between the first electrode and the second electrode.

10. The timing device of claim 9, wherein the current source is configured to detect operation of an electronic device and to apply the current between the first electrode and the second electrode while the electronic device is in operation such that the growth of the electrodeposit is indicative of a total run-time of the electronic device.

11. The timing device of claim 10, wherein the current source includes an antenna configured to receive electromagnetic radiation emitted from a chip clock of the electronic device and to apply a current derived from the received electromagnetic radiation as the current applied between the first electrode and the second electrode.

12. The timing device of claim 1, wherein the current source is configured to operate the timing device as an activation fuse for a system by applying a constant current or a periodic pulsed current between the first electrode and the second electrode.

13. The timing device of claim 1, further comprising a channel positioned between the first electrode and the second electrode and configured such that the electrodeposit forms on the first electrode towards the second electrode within the channel.

14. A timing device comprising:
a first electrode;
a second electrode;
an electrolyte positioned between the first electrode and the second electrode, the electrolyte including a material selected such that an electrodeposit forms on the first electrode when a current is applied between the first electrode and the second electrode,
wherein a measureable electrical characteristic of the timing device is indicative of a time-dependent degree of growth of the electrodeposit between the first electrode and the second electrode,
wherein a resistivity of the electrolyte is higher than a resistivity of the electrodeposit, and wherein the measurable electrical characteristic indicative of the time-dependent degree of growth of the electrodeposit includes a resistance between the first electrode and the second electrode; and
further comprising a controller configured to:
detect an expiration of a first timing interval when a resistance between the first electrode and the sense electrode falls below a first resistance threshold, and
detect an expiration of a second timing interval when a resistance between the first electrode and the second electrode falls below a second resistance threshold.

15. A method of operating a timing device, the method comprising:
applying a current between a first electrode and a second electrode, the first electrode and the second electrode being coupled by an electrolyte including a material that causes an electrodeposit to form on the first electrode when the current is applied;
monitoring a resistance between the first electrode and the second electrode, wherein the resistance is indicative of growth of the electrodeposit between the first electrode and the second electrode;
detecting expiration of a timing interval based on a threshold of the monitored resistance; and
generating an output timing signal indicative of the expiration of a timer when the threshold is exceeded.

16. The method of claim 15, further comprising adjusting a rate of growth of the electrodeposit by adjusting a magnitude of the current applied between the first electrode and the second electrode.

17. The method of claim 16, wherein applying the current includes applying a periodic pulsed current, and further comprising adjusting a rate of growth of the electrodeposit by adjusting a frequency or a pulse width of the period pulsed current.

18. The method of claim 15, further comprising:
coupling the timing device to an electronic device such that the current between the first electrode and the second electrode is applied when the electronic device is operating; and
monitoring a total run-time of the electronic device based on the output signal from the timing device indicative of the growth of the electrodeposit.

* * * * *